United States Patent [19]

Ellebracht

[11] Patent Number: 4,617,828

[45] Date of Patent: Oct. 21, 1986

[54] METHOD AND APPARATUS FOR DETERMINING THE SOLUBILITY OF VOLATILE MATERIALS IN NON-VOLATILE MATERIALS

[75] Inventor: Stephen R. Ellebracht, Lake Jackson, Tex.

[73] Assignee: The Dow Chemical Company, Midland, Mich.

[21] Appl. No.: 717,401

[22] Filed: Mar. 29, 1985

[51] Int. Cl.$^4$ .............................................. G01N 7/00
[52] U.S. Cl. ...................................................... 73/866
[58] Field of Search ............ 73/432 Z, 863.21, 864.83, 73/864.84, 864.71, 19, 23.1, 432 R

[56] References Cited

U.S. PATENT DOCUMENTS

| | | | |
|---|---|---|---|
| 3,185,820 | 5/1965 | Williams et al. | 73/23.1 |
| 3,286,530 | 11/1966 | Ayers | 73/23.1 |
| 4,154,086 | 5/1979 | Button et al. | 73/19 |
| 4,496,433 | 1/1985 | Annino et al. | 73/23.1 |

Primary Examiner—Stewart J. Levy
Assistant Examiner—Robert R. Raevis
Attorney, Agent, or Firm—M. W. Barrow

[57] ABSTRACT

Method and apparatus for determining solubilities of gases and mixtures of gases in polymeric material at various temperature and pressure conditions. Employs means for saturating polymer with a gas, means for desorbing the sorbed gas by a flowing desorbing gas stream, means for sampling the desorbing gas stream and detecting the concentration of the desorbed gas in the desorbing gas, and means for calculating the total amount of gas desorbed from the polymeric material.

11 Claims, 1 Drawing Figure

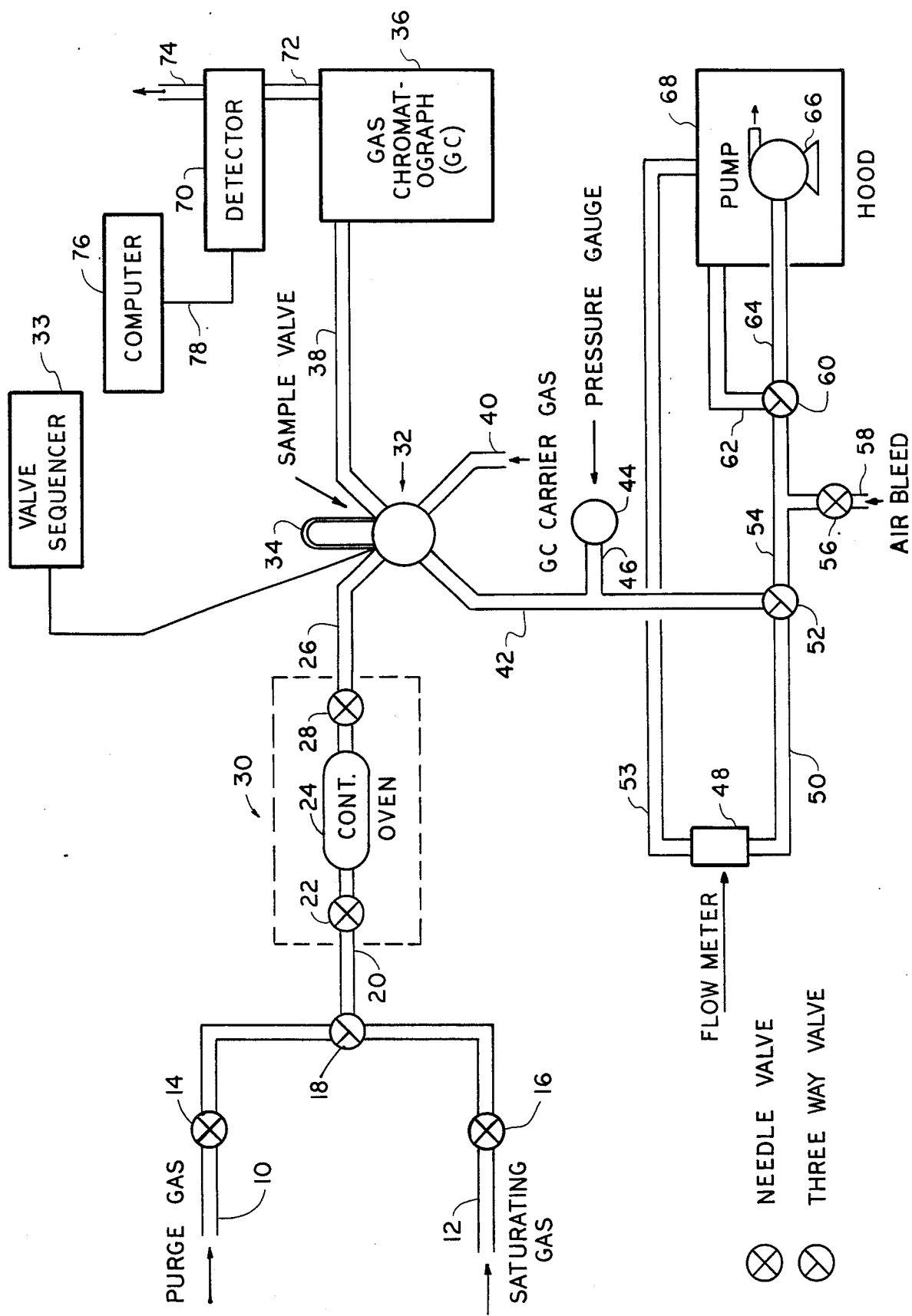

METHOD AND APPARATUS FOR DETERMINING THE SOLUBILITY OF VOLATILE MATERIALS IN NON-VOLATILE MATERIALS

BACKGROUND OF THE INVENTION

1. Field of the Invention

This invention relates to the measurement of the solubility of volatile materials in non-volatile materials. It is particularly suitable for measuring the solubility of the volatile monomers and incompletely reacted partial polymeric material contained in synthetic polymers which are manufactured by reacting monomers. This solubility information is useful in designing separation stages for removal of the unreacted monomers and incompletely reacted polymeric material from the satisfactorily reacted polymeric material.

2. Definitions Used Herein

Definitional problems occur when trying to fit all matter into either the three widely known states used by laymen, i.e., solid state, liquid state, or gaseous state. Many materials just do not clearly fit any one state, e.g., what state do warm butter or warm tar fit into? To avoid many of these difficulties, herein states of matter will be designated as either volatile material or non-volatile material. These will be distinguished by the following definitions:

a. Volatile materials shall be those materials whose vapor pressure is greater than the pressure of the specific temperature and pressure condition at which the solubility of the volatile material within the non-volatile material is desired to be known. Synonyms for volatile materials as used herein are gases, volatiles, gaseous monomers, gaseous oligomers, gaseous solvents, and similar words; and b. Non-volatile material shall be material whose vapor pressure is less than the pressure of the specific temperature and pressure condition at which the solubility of the volatile material within the non-volatile material is desired to be known. Synonyms for non-volatile materials are non-volatiles, solids, liquids and polymers.

Another concept of definite meaning, but often difficulty of proving its precise existence, is "solubility". However, those skilled in the art of polymeric materials use the word interchangeably with the more broader word, "sorbed". Therefore, herein the word "solubility" shall mean "sorb", and "dissolved" materials shall mean "sorbed" materials. Hence, herein in determining the solubility of volatile materials in non-volatile materials at a specific temperature and pressure condition, the determination shall mean the extent to which the volatile materials can be sorbed by the non-volatile materials at that specific temperature and pressure condition.

DISCUSSION OF PRIOR ART

The prior art recognizes the commercial significance of being able to know the actual amount of unreacted gaseous monomers dissolved or sorbed within a solid or highly viscous polymer made from the monomers. E.g., Maloney, D. P. and Prausnitz, J. M., "Solubilities of Ethylene and Other Organic Solutes in Liquid, Low-Density Polyethylene in the Region 124° to 300° C.", *AIChE Journal*, vol. 22, no. 1, p. 74 et seq. (Jan., 1976); Mlejnek, O., "Analysis of Volatiles in Polymers by Gas Chromatography", *Journal of Chromatography*, vol. 65, pp. 271–277 (1972); Meyer, J. A., "Quantitative Determination of Volatiles in Non-Volatile Matrices," *Journal of Chromatography*, vol. 99, pp. 709–720 (1974); Romano, S. J. Renner, J. A. and Leitner, P. M., "Gas Chromatographic Determination of Residual Ethylene Oxide by Head Space Analysis," *Analytical Chemistry*, vol. 45, no. 14, pp. 2327–2330 (Dec. 1973); Maloney, D. P. and Prausnitz, J. M., "Solubility of Ethylene in Liquid, Low-Density Polyethylene at Industrial Separation Pressures," *Industrial Engineering Chemistry, Process Design Development*, vol. 15, no. 1, pp. 216–220 (1976).

However, the prior art does not contain a quick, simple method and apparatus for directly measuring the solubility of volatile gases in polymeric solids. These prior art methods require the use of assumptions or extrapolations which are of considerable value but which are lacking in the certainty which commercial producers favor. For example, the article by Maloney and Prausnitz cited above described a method and apparatus for measuring the solubilities of organic solutes in polyethylene which is hot enough to be in liquid form. This article teaches that the desired solubilities can be determined from a complicated mathematical formula involving many variables. Many assumptions have to be made in using this formula.

The Mlejnek article cited above teaches introducing samples to an ampoule which is then sealed and brought to the desired conditions of temperature and pressure. The ampoule is then opened in a sampling system which enables the volatile components to be determined as a method of measuring the solubility volatiles in non-volatile material. This way is deficient in that sealing and breaking ampoules is cumbersome and limits the flexibility of the experiment. It also does not allow any extra gas to be present in the ampoule as the temperature and pressure are changed after the ampoule is sealed.

The Meyer article cited above teaches using an integrated vacuum distillation-gas chromatography method as a method of determining the solubility of volatiles in non-volatiles. This method is deficient in that it provides no means for setting the desired conditions of pressure, temperature and absorbing gas.

The article of Romano et al. cited above teaches analyzing the headspace of a sample as a method for determining the solubility of ethylene oxide in dimethylformamide. This method is deficient in that it is limited to relatively low boiling hydrocarbon volatiles and has no means for setting proper conditions of absorbent concentration, sample temperature or pressure.

The article by Maloney and Prausnitz cited above teaches using gas-liquid chromatography along with a complicated set of correction equations as a method for measuring the solubility of ethylene in liquid, low-density polyethylene at production pressures. This method is deficient in that it is too complicated and involves too many assumptions to be a quick and easy way to make these determinations.

The present invention overcomes these and other disadvantages as will be appreciated by those skilled in the art.

SUMMARY OF THE INVENTION

The present invention is a method and an apparatus for directly measuring the solubility of volatile materials in non-volatile materials. The invention accomplishes this measurement by saturating a sample of a non-volatile material with a headspace gas stream of the volatile material in an enclosed container; sweeping the non-dissolved, non-sorbed headspace gas out of the container; desorbing the dissolved volatile gas from the non-volatile material into a flowing stream of desorbing gas; measuring the amount of this formerly dissolved volatile gas now contained in the desorbing gas; and dividing this amount of measured volatile gas by the amount of non-volatile material in which this volatile gas was previously dissolved inside the container.

STATEMENT OF THE INVENTION

The present invention is a method and apparatus for making a direct, relatively quick determination of the solubility of volatile materials in substantially non-volatile materials at variously desired temperatures and pressures. Normally the most advantageous use of this invention occurs when the non-volatile material is a synthetic polymeric material and the volatile material includes an organic material which is used in the manufacture of the synthetic polymeric material. Usually the volatile material includes unreacted monomers, and incompletely reacted polymeric material, from the satisfactorily reacted polymeric material. The non-volatile synthetic polymeric material is often a monomer or copolymer. For example, the non-volatile synthetic polymeric material is often a copolymer made from ethylene and an alpha olefinic copolymer selected from the group comprised of $C_3$ through $C_{12}$ olefins. Ethylene-butene copolymer is a specific example of the non-volatile polymeric material being a copolymer. Polyethylene is a specific example of the non-volatile polymeric material being a monomeric polymer. Other examples of non-volatile polymeric materials are polycarbonates polyurethane, and epoxy resins. ABS is also an example of such non-volatile polymeric materials. An example of volatile materials is the unreacted, and partially reacted, ethylene used and produced in the manufacture of the non-volatile polyethylene monomeric polymer. Another example of volatile materials are the unreacted, and partially reacted, ethylene and 1-butene used in the manufacture of the non-volatile ethylenebutene copolymer. Often, the volatile material is some mixture of hydrocarbon gases used in the manufacture of a non-volatile polymeric material.

The method comprises a few steps. First the non-volatile material, usually a synthetic polymeric substance, is placed in a container. Then it is saturated with the volatile material or gases whose saturation amount in the non-volatile material is desired to be known. This saturation is carried out by flowing a stream of this saturating gas through the container and contacting it with the non-volatile material until the non-volatile material becomes saturated with the saturating gas. This saturation of the non-volatile material is carried out with the temperature and pressure of the materials inside the container being maintained at the particular temperature and particular pressure at which the solubility of the volatile material in the non-volatile material is desired to be known.

The next step in this method is to stop the flow of saturating gas and then remove all volatile materials from the container which are not sorbed by the non-volatile material. This is done by flowing a purge gas stream through the container at a sufficiently large flow rate and for a sufficient time to essentially purge the container of any non-sorbed volatile material remaining free in the container. However, this purge gas flow should be for a sufficiently short time so as not to appreciably reduce the amount of volatile materials sorbed by the non-volatile material located within the container. The purge gas and container contents should be maintained at the same temperature and pressure as the pressure and temperature at which the solubility of the volatile materials in the non-volatile materials is desired to be known. The purge gas should be one which is essentially chemically inactive at least with the non-volatile and volatile materials. Nitrogen or helium are the usual purge gases of choice for most purposes.

The only saturating gas, or volatile material, which remains in the container is that which is sorbed in the non-volatile material.

This sorbed volatile material is then transferred from the non-volatile material to a desorbing gas. This is done by flowing the desorbing gas in a stream through the container in a manner so as to contact the non-volatile material for a time sufficient for essentially all of the volatile material sorbed in the non-volatile material to transfer from the non-volatile material to the desorbing gas stream. This desorbing gas must be virtually chemically inert with respect to the volatile material at the temperature and pressure of interest. The temperature and pressure of the contents of the container should be maintained at the temperature and pressure at which the solubility of the volatile material in the non-volatile material is desired to be known.

The desorbing gas is usually the same kind of gas as the purge gas. In fact they preferably come from the same source and are transferred to the container by the same means. Usually the only difference between the purge gas and the desorbing gas is what happens to them.

Ultimately the desorbing gas, or incremental parts thereof, must pass through a detector located downstream from the container. With the detector, the desorbed volatile material contained in the desorbing gas can be measured and used in the determination of the solubility of the volatile material in the non-volatile material. Of course, if the purge gas stream, or parts thereof, also goes through the detector, then the volatile material contained in the purge gas should not be used in the determination of the solubility as it was never dissolved or sorbed by the non-volatile material. It was discovered that substantially all of the non-sorbed volatile gas in the container could be swiftly swept from the container by the purge gas stream before there ocurred any significant desorption of sorbed volatile gas from the non-volatile material for most materials. Choosing the amount of time it takes to clear the container of undissolved volatile gas materials can be determined in several ways. Probably the easiest and surest way to do this is to measure how long it takes to sweep a container free of volatile material when the container has no non-volatile material in it and it was originally filled with volatile material.

Needless to say, this invention will not work very well if there is a significant overlap of time before the container can be swept essentially free of unsorbed material before any significant amount of the dissolved volatile material starts desorbing from the non-volatile material into the container. But usually the purge gas flow rate can be increased sufficiently to overcome this problem, and usually there is no problem.

As can be readily appreciated, this invention can also be used to determine effusion rates of volatile material sorbed by non-volatile materials from these non-volatile materials.

The next step is the determination of the total amount of the volatile gases or material now contained in the desorbing gas stream. The total volume of desorbing gas can be passed through the container and collected in a vessel for later measurement and calculation of the desired solubility. However, it is preferred to measure and calculate this solubility as the desorbing gas stream flows from the container. The determination of the total amount of volatile gases contained in the desorbing gas stream can be accomplished by taking several small samples of known volumes from the desorbing gas stream at intermittent times after the desorbing gas stream emerges from the container, and then passing these incremental samples on through a gas chromatograph and detector as they are collected. The gas chromatograph employs a detector which is sensitive to the volatile materials but not to the desorbing gas.

The detector produces several measurements with each one giving the amount of volatile gas contained in each of the small samples intermittently taken from the desorbing gas stream. These several amounts can then be plotted on a two-dimensional graph with one axis representing time and the other axis representing the amount of volatile material contained in each of the small samples. The area under the curve with respect to the time axis, i.e., the curve integrated with respect to the time axis, will be a very close approximation of the total amount of volatiles contained within the desorbing gas, and hence will be a very close approximation of the solubility of the volatile material in the non-volatile material in the container; that is, it will be a very close approximation if three variables are considered and accounted for. First, the time between the small sample taking from the purge gas must be the same as that plotted on the graph. The easiest way to avoid error in this respect is simply to run each sample taken from the purge gas directly and immediately into the gas chromatograph with a timer clock noting the time of the peaks produced by the chromatograph detector as they occur.

Secondly, an accommodation must be made for the sizes of the small samples taken from the desorbing gas stream. If they are not the same size, then their individual sizes must be known and made equivalent in order to produce a graph whose integration will produce a value which is truly representative of the amount of volatile gases contained within the desorbing gas stream. For example, if one small sample is twice the amount of the rest of the small samples taken from the desorbing gas stream, then the amount of volatiles in the larger of the samples would have to be reduced by one-half before it was plotted on the graph. Of course, the easiest way to handle such a reconciliation of small sample volumes is to have all the small samples be of the same volume.

The third variable is the flow rate of the desorbing gas stream. If this flow rate is variable then several reconciliations have to be made to obtain an integrable curve on the graph which would be representative of the total amount of volatile materials contained in the desorbing gas stream. Hence, it is simplest merely to keep the desorbing gas flow at a constant rate.

Of course, the curve which can be generated from these measurements need not be actually made, but can be, and most often is preferable to be, present only in representative form in a computer. The integration of the curve is preferably done also by a computer.

The integration of the curve gives the total amount of volatile material present in the desorbing gas stream, and, hence, it also gives essentially the total amount of volatiles dissolved in and/or sorbed by the non-volatile material in the container. Therefore, all that is left to do in order to determine the solubility of the volatile materials in the non-volatile material in the container is to divide the amount of volatile material by the amount of non-volatile material in the container. This amount to amount division can be on a weight to weight basis, a volume to volume basis, a volume to weight basis, or a weight to volume basis, or any other desired basis. Most often, however, solubilities are measured on a microgram to gram basis.

As to the apparatus of this invention, generally speaking it is comprised of the several means required to carry out the several steps of this invention as described above. Thus it includes a sealable container into which the non-volatile material can be placed. The container has a gas inlet and a gas outlet by which gas can be flowed into, through, and on out of the container in a manner such that the gas comes into substantial contact with the non-volatile material when it is located inside of the container. The preferred container is a small glass or stainless steel tube with one end being its inlet and the other end being its outlet.

This apparatus includes a means for flowing a gaseous saturating stream of the volatile material through the container via its gas outlet and its gas outlet at the temperature and pressure at which the solubility of the volatile material in the non-volatile material is desired to be known. This flow is continued for a sufficient time for the non-volatile material to become virtually totally saturated with volatile material sorbed from this flowing gas stream.

The apparatus necessarily has a means for stopping the flow of the saturating stream through the container in order that the volatile material sorbed by the non-volatile material may be desorbed from it.

Before this desorption is set about, however, the container must be first purged of residual volatile gaseous material which remains in the container but which is not sorbed by the non-volatile material. This purging is accomplished by employing means for flowing a purge gas stream through the container at a sufficiently large flow rate for a sufficient time to sweep the container essentially free of any non-sorbed volatile materials remaining in the container, but flowing this high flow rate purge gas stream in a sufficiently short time so as not to appreciably reduce the amount of volatile materials which are sorbed by the non-volatile material present in the container. This purge gas should be a gas which is substantially non-reactive with the volatile material and otherwise relatively inert. Nitrogen or helium gases are usually the most practical to use.

The apparatus must also include a means for flowing a desorbing gas stream through the container via its gas inlet and gas outlet in a manner and for a time sufficient so that the desorbing gas stream is in contact with the non-volatile material for a sufficiently long time so that substantially all of the volatile materials which were previously sorbed by the non-volatile material are desorbed from the non-volatile material and picked up by the flowing desorbing gas stream. The means for flowing this desorbing gas stream flows the desorbing gas at a known flow rate. This desorbing gas should be one which is virtually chemically inert to the volatile materials it desorbs. Preferably it is inert to all materials it contacts within the apparatus. Nitrogen or helium are usually the more practical gases to use.

Of course, the gas used as purge gas can also often be the same kind as that used for the desorbing gas. Furthermore, the means for flowing the purge gas can be the same means as that used for flowing the desorbing gas.

The apparatus of the invention further includes a means for intermittently taking small samples of known volume from the desorbing gas stream after it, the desorbing gas stream, has exited the container. These known small samples are flowed through a gas chromatograph which is also part of the apparatus of this invention. The apparatus has a detector associated with the gas chromatograph which is sensitive to the volatile material in the desorbing gas but which is not significantly sensitive to the desorbing gas itself.

This apparatus also includes means for taking samples from the detector which represent the amount of volatile material being detected by the detector and computing the amount of volatile material desorbed from the non-volatile material.

BRIEF DESCRIPTION OF THE DRAWINGS

A better appreciation of the invention will be obtained by reference to the drawing which is a schematic view showing the preferred parts and flow paths of the gases during the several steps of the process.

DISCUSSION OF THE PREFERRED EMBODIMENT

The object of this invention is to directly measure to solubility of volatile gas or gases in non-volatile materials.

In the drawing a schematic outline is set forth which shows the equipment and gas flow direction when a piece of the non-volatile material is maintained in a container 24 and the volatile gas or gases are flowed around and in contact with the non-volatile material for a sufficient time to saturate the non-volatile material with the volatile gas or gases.

A list of the equipment represented in the drawing along with each element's respective reference numbers, is as follows:

| Reference Numbers | Equipment |
|---|---|
| 10 | Purge gas line |
| 12 | Saturating gas line |
| 14 | Purge gas line needle valve |
| 16 | Saturating gas line needle valve |
| 18 | Air actuated sample switching valve |
| 20 | Container inlet line |
| 22 | Container feed line needle valve |
| 24 | Sample container |
| 26 | Container outlet line |
| 28 | Container outlet line needle valve |
| 30 | Container oven |
| 32 | Six-port sample injection valve |
| 33 | Computer programmed valve sequencer |
| 34 | Small sample volume loop line |
| 36 | Gas chromatograph |
| 38 | Gas chromatograph feed line |
| 40 | Gas chromatograph carrier gas line |
| 42 | Sample valve exhaust line |
| 44 | Pressure gauge |
| 46 | Pressure gauge line |
| 48 | Flow meter |
| 50 | Line |
| 52 | Switching valve |
| 53 | Flow meter exit line to hood |
| 54 | Line |
| 56 | Air bleed needle valve |
| 58 | Air bleed line |
| 60 | Three-way valve |

| Reference Numbers | Equipment |
|---|---|
| 62 | Vacuum pump bypass line |
| 64 | Vacuum pump feed line |
| 66 | Vacuum pump |
| 68 | Laboratory safety hood |
| 70 | Detector |
| 72 | Gas Line |
| 74 | Exhaust vent |
| 76 | Computer |
| 78 | Electrical coupling |

In this preferred embodiment, the purge gas and the desorbing gas are the same and so is their flow path. Therefore, reference to elements of the purge gas flow path is also reference to elements of the desorbing gas flow path. Thus when reference is made to a purge gas flow path element, it is to be understood that that element is also a desorbing gas flow path element.

Purge gas line 10 and saturating gas line 12 are connected to line 20 through switching valve 18. Line 10 has needle valve 14 in it, line 12 has needle valve 16 in it, and line 20 has needle valve 22 in it. Line 20 serves as a gas feed line to non-volatile sample container 24. Container 24 is a glass or metal tube into which a non-volatile sample of polymer is placed before the container 24 is connected to lines 20 and 26, and maintained under various pressures and temperatures accordingly as desired. Container 24 is maintained in oven 30 so that container 24 and its contents can be maintained at some constant, desired temperature. Container 24 is placed in fluid connection with switching valve 32 via line 26 when needle valve 28 is open.

Valve 32 is a six-port air actuated switching valve. It is switched from port to port by computer programmed valve sequencer 33. Connected to two of the six ports of valve 32 is a constant volume sample tube loop 34. Also connected to switching valve 32 are lines 38, 40 and 42. Line 38 is used for transferring gas from valve 32 to gas chromatograph 36. Line 40 is used to transfer a gas chromatograph carrier gas through valve 32, through line 38, and through gas chromatograph 36 as it is needed. Line 42 is used as an exhaust line from valve 32.

The pressure in line 42, and thus also the pressure back in container 24, is monitored by pressure gauge 44. Gauge 44 is connected to line 42 by line 46. Likewise the flow rate of fluid through lines 42 and 54, and consequently through container 24, is carefully monitored by flow meter 48. As can be seen, flow meter 48 is connected to lines 42 and 54 via line 50 through three-way valve 52. The pressure and flow rate of the desorbing gas, the purge gas and the saturating gas in and through container 24 is controlled by needle valves 14, 16, 22, 28 and three-way valve 18.

Flow meter 48 is in fluid communication with line 42 through line 50 and further on through three-way valve 52, that is when valve 52 is open between line 50 and line 42. Flow meter 48 exhausts into safety hood 68 through line 53.

Line 42 is in fluid communication with line 54 when valve 52 is turned appropriately. When it is desired that the gas flowing through container 24, line 26, valve 32, line 42, valve 52 and line 54 be at a pressure which is greater than atmospheric pressure, then valve 56, line 58, line 64 and the vacuum pump 66 are not used. In this situation the gas can be vented directly into safety hood 68 through valve 60 and line 62, and then it can be suitably exhausted to the atmosphere therefrom.

However, when the pressure of this gas is desired to be less than atmospheric pressure, then the vacuum pump 66 and line 64 need to be employed in order to vent the gas into safety hood 68. When operating at sub-atmospheric pressure it has been found useful to employ air bleed line 58 and needle valve 56 because vacuum pump 66 often pulls such a large vacuum that control of the desire vacuum pressure is difficult to obtain and maintain. This difficulty is alleviated by allowing air to bleed into line 54 from the atmosphere through line 58 and needle valve 56. Precise control of this air bleed flow rate is accomplished by turning needle valve 56 until the precise, desired, subatmospheric pressure desired in container 24 is observed at pressure gauge 44.

In operation the above described system works in an essentially three-mode system: (a) the non-volatile material saturating mode; (b) the non-sorbed volatile material purging mode; and (c) the sorbed volatile material desorbing mode.

A. NON-VOLATILE MATERIAL SATURATING MODE

In the non-volatile material saturating mode a piece of the non-volatile material to be saturated is placed within container 24 with valves 22, 28 closed. Valves 22 and 28 are then opened. Also in this mode: valve 16 is open; valve 14 is closed; three-way valve 18 is open between line 12 and line 20 to allow saturating gas to pass therethrough; three-way valve 52 is open between line 42 and line 54 to allow saturating gas to flow therethrough; and three-way valve 60 is either open to line 62 or open to line 64 depending on whether the pressure of the saturating gas is, respectively, above atmospheric pressure or below atmospheric pressure. Valve 60 is open to line 62 when the pressure in it is at, or above, atmospheric pressure. Valve 60 is open to line 64 and vacuum pump 66 when this pressure is less than atmospheric pressure. The position of valve 56 will also depend upon the pressure of the flowing saturating gas as discussed above for air bleeding when the line pressure is below atmospheric pressure.

The six-port sample injection valve 32 is in a position so that saturating gas from line 26 flows directly into line 42 through valve 32 without passing through line 34 or line 38. During this mode of operation there is a carrier gas for the gas chromatograph 36 being flowed from line 40 through valve 32, line 34, valve 32, and line 38. Thus during this mode of saturating, the piece of non-volatile material enclosed within container 24 can have the volatile material (i.e., saturating gas) flow over it until the piece of non-volatile material has sorbed enough of the volatile material to become saturated with it. The temperature of the contents in the container 24 are maintained at the desired temperature using oven 30. The desired pressure is maintained as described above using needle valves 16, 22 and 28.

B. MODE OF PURGING THE NON-SORBED VOLATILE MATERIALS FROM THE CONTAINER

The purpose of this mode is to remove all of the non-sorbed volatile gas within the container and in the remainder of the system between valve 18 and the detector 70 before any significant amount of sorbed volatiles can be desorbed from the non-volatile material in container 24. To accomplish this, switching valve 18 is switched so that purge gas line 10 is now the line in fluid communication with line 20 instead of saturating (volatile) gas line 12, with needle valve 14 being already previously set open the correct amount to obtain the proper flow rate through and pressure within container 24. The remainder of the valves remain as they were during the first mode of operation described above. Thus the purging gas follows the same flow path as did the saturating gas stream.

C. MODE OF DESORBING THE SORBED VOLATILE MATERIAL FROM THE NON-VOLATILE MATERIAL

The purpose of this mode is to measure the total amount of volatile material contained in the non-volatile material.

The flow of gas in this mode is as follows. The saturating gas flow remains cut off by valve 18, and valve 18 continues to allow the flow of purge gas from line 10 into line 20. Of course, the purge gas is now acting as a desorbing gas to desorb sorbed volatile materials from the non-volatile material in the gas stream, but it will still be often referred to as the purge gas, as mentioned above. The purge gas flows as follows: through line 10, valves 14 and 18, line 20, valve 22, container 24, line 26 and valve 28, and into six-port rotary switching valve 32. So far this route is the same as that for the saturating gas in the first operating mode above, that is the same downstream from valve 18 to sample valve 32. However, in this desorbing mode, sample valve 32 switches back and forth between two different positions so that the desorbing gas flow is flowing through at least part of a different flowpath than did the saturating gas.

Switching sample valve 32 is caused to be switched back and forth by valve sequencer 33 between a sample collecting mode and a sample injection mode. In the sample collecting mode, the purge gas flows into valve 32 from line 26, out of valve 32 into fixed volume sample loop 34, back into sample valve 32 from loop 34, and out of valve 32 into line 42. From line 42, the purge gas follows the same path into the laboratory hood 68 as did the saturating gas described above. In the meantime carrier gas for the gas chromatograph is flowing into sample valve 32 from line 42, out of sample valve 32 into gas chromatograph 36 via line 38, through gas chromatograph 36 and out of it through line 72, from line 72 into and through detector 70, and on to exhaust through exhaust vent 74.

In the sample injection mode, valve sequencer 33 causes the sample of gaseous material happening to be flowing in sample loop line 34 to be abruptly injected into line 38 on its way to gas chromatograph 36 and detector 70. This is done by rotating sample valve 32 until the inlet and outlet of sample loop line 34 are in line with lines 40 and 38, respectively. In this position the carrier gas flowing in line 40 forces the purge gas sample caught in sample loop 34 into line 38, on through gas chromatograph 36, through line 72, through detector 70, and out through exhaust line 74. The volatile material captured in this incremental fixed volume of purge gas is sensed as to time and amount by detector 70. Electrical signals corresponding to these times and amounts are sent from detector 70 to computer 76 via electrical coupling 78.

While sample valve 32 is in this sample injection position, the purge gas continues to flow from container 24 and through sample valve 32, but now it is flowing directly through sample valve 32 into line 42 without flowing through small sample volume loop line 34, and then on eventually into hood 68, as did the saturating gas.

Valve sequencer 33 then switches sample injection valve 32 back to the sample collecting mode for reloading of sample loop 34. Then valve sequencer 33 switches sample injection valve 32 back again into the sample injection mode wherein a second sample of desorbing gas from sample loop 34 is transferred through gas chromatograph 36 and detector 70. This switching of sample valve 32 continues until essentially all of the volatile material sorbed by the non-volatile material has been desorbed from the non-volatile material into the desorbing gas stream.

The temperature and pressure of all the material inside container 24 is kept at constant level during all the above described flowing of gases through container 24 during all three of the above described operating modes, i.e., (a) the non-volatile material saturating mode, (b) the non-sorbed volatile material purging mode, and (c) the sorbed volatile material desorbing mode. The flow rate of gas is kept constant during the flow of the saturating gas through container 24, the flow rate of the purge gas is kept constant while it is flowing, and the flow rate of the desorbing gas is kept constant during the time it is flowed through container 24.

Knowing when to switch from the pure purge mode to this desorbing mode is a matter of trial and error learning of timing inasmuch as some of the sorbed material starts desorbing from the non-volatile material into container 24 as soon as the non-sorbed volatile gas is started to be displaced from the container 24 by the purge gas. Thus, this displacement needs to take place sufficiently fact so that it will be essentially completed before any significant amount of sorbed volatile gas has become desorbed from the non-volatile material. It should be remembered that detector 70 is chosen to be sensitive to all the volatile materials, but not to the purge gas. Therefore detector 70 will be unable to distinguish between volatile materials which have been desorbed from the non-volatile material and that which was never sorbed by the non-volatile material. Thus, it is important to know how quickly the non-sorbed volatile materials can be removed from container 24, lines 20 and 26 and valve 32, and it is important to know how soon it is before there is a significant amount of desorption of the sorbed volatile materials from the non-volatile materials in container 24. These times, of course, need to be determined for each different kind of solubility test.

One way to determine these two times is to first find out how fast it takes to purge container 24, lines 20, 26, and valve 32 of volatile material when container 24 is filled only with volatile materials while taking measurements of this amount; i.e., when container 24 has no non-volatile material sample in it so that all of its volume was filled with volatile material. It is also important to determine the amount of volatile material contained in container 24, lines 20, 26 and valve 32 when testing the system to see how fast these elements can be cleared when container 24 has no sample of non-volatile material in it. This is done by sampling the purge gas when purging container 24 with sample valve 32, flowing these samples through gas chromatograph 36, flowing the sample of gas through detector 70 via line 72, detecting the presence and amount of volatile materials in the purge gas samples by detector 70, sending electrical signals which are proportional to these amounts to computer 76 via electrical coupling 78, and computing the total amount of volatiles contained in line 20, 26, container 24, and line 26 and value 32 as well as graphing the time it took to remove all but an insignificant amount of the volatile gas from these elements. A curve is also plotted of the amount of volatile gas versus the time it took to remove it.

The time it takes before significant amounts of sorbed volatile materials are desorbed from a non-volatile material sample in the container is determined by following the same procedure as determining the time it takes to remove the non-sorbed gas from container 24, lines 20, 26, and valve 32. In this type of run, however, there will be a time lag displayed on the graph of the volatile materials versus time graph generated by the computer between the time significant amounts of non-sorbed volatile material are detected and the time formerly sorbed volatile materials are detected.

Thus in calculating the solubility of a volatile material in a non-volatile material, the purge gas is turned on, and samples of it are run through the detector 70, and then only the amount of volatile materials which are attributable to being desorbed from the non-volatile material is calculated by the computer 76.

In actual running of the computer, of course, it is not necessary for the computer to physically make a graph of volatile materials detected versus time and then integrating it to determine the amount of volatile materials detected. This graphing and integration can all be done electronically within the computer.

EXAMPLE

A three-gram sample (a good trade-off between a sample which is too small to give good reproducibility and one which is too large to allow a reasonable desorption time) of ethylene-butene copolymer was weighed and placed into a ten-milliliter sample bomb (container 24 in the drawing). The bomb was made of stainless steel. The bomb 24 was then placed into an oven controlled at $150\pm0.5°$ C. and connected to the inlet and outlet lines 20, 26 as shown in the drawing. The bomb 24 was placed in a horizontal position in the oven to keep the molten copolymer from sliding to one end and plugging the bomb's outlet port. A saturating gas mixture stream of 12.6% ethylene and 87.4% butene was then flowed through the bomb 24 from line 12 using the three-way valve 18. A desired pressure of 3 psia ($2.69\times10^{43}$ pascals) was set for the gas mixture stream in the bomb container 24 using pressure gauge 44, needle valves 16, 22, 28 and vacuum pump 66. The oven temperature was monitored with a digital readout thermocouple. A slight flow of the saturating gas mixture of 12.6% ethylene and 87.4% butene of about 1 to 2 milliliters/minute was flowed through the bomb container 24 to assure proper gas concentration in the headspace above the ethylene-butene copolymer sample in the bomb container. This flow was continued for 16 hours in order to give the sample of copolymer sufficient time to be saturated with ethylene and butene from the gas mixture.

After equilibrium was reached for the saturation, the three-way valve 18 was used to switch the flow through the bomb 24 from the slow ethylene-butene saturating gas flow to a faster 100 milliliter/minute flow of helium gas. At the same time, the valve sequencer 33, the comparator 76, and the gas chromatograph recorder (not shown) were activated. The first 15 seconds were used to purge the system of ethylene and butene gas which had not been sorbed by the polymer sample. After 15 seconds the valve sequencer 33 started rotation of the sample injection valve 32 so that it was sending gas samples through gas chromatograph 36 and detector 70 with detector 70 sending signals of the amounts of ethylene and butene to computer 76 contained in each sample. Computer 76 integrated these signals to give the solubility of the ethylene-butene mixture in the ethylene-butene polymer to be 5 ppm for the ethylene and 1110 ppm for butene under the conditions used.

To desorb the entire polymeric sample of sorbed butene and ethylene took about 250 minutes. However, it was discovered that after about 20 minutes the computer had enough data points to extrapolate a correct curve describing the total desorption. Hence, for the given conditions the actual data collection can be stopped after about 20 minutes with the computer still being able to give an accurate solubility reading for the ethylene and butene.

What is claimed:

1. A method of measuring the solubility of volatile materials in non-volatile materials at specified temperature and pressure conditions, said method being comprised of the steps of:
    a. placing a sample of substantially solid non-volatile material inside a container which has sufficient volume to allow gases to flow through the container while contacting the non-volatile material and which has a gas inlet and a gas outlet by which gas can, respectively, flow into and out of the container;
    b. flowing a gaseous saturating stream of a volatile material through the container in a manner so as to contact and be sorbed by the non-volatile material for a time sufficient for the non-volatile material to become virtually saturated with volatile material while maintaining the temperature and pressure of all material within the container at predetermined constant conditions;
    c. stopping the flow of the saturating stream of volatile material;
    d. flowing a purge gas through the container at a sufficiently high flow rate to substantially purge the container of its non-sorbed volatile materials but in a sufficiently short time so as not to appreciably reduce the amount of volatile materials sorbed by the non-volatile material, said purge gas being one which does not contain any of the volatile materials of the saturating stream in any significant amount as well as being one which is not reactive in any significant amount with the volatile or non-volatile materials under the conditions used in this method;
    e. continuously flowing a desorbing gas stream which has the same properties as those defined for the purge gas in step (d) above through the container in a manner and for a sufficient time so that the gas of the stream contacts the non-volatile material for a time sufficiently long so that substantially all of the volatile materials previously sorbed by the non-volatile material are desorbed from the non-volatile material into the flowing desorbing gas stream, said desorbing gas stream flow being maintained at a known flow rate so that the effect of its flow rate can be accounted for and disregarded in determining the amount of volatile material transferred to it from the non-volatile material per unit of time in the following steps;
        1. periodically taking incremental samples of known volumes from the desorbing gas stream flowing from the container;
        2. flowing these known volume samples on through a gas chromatograph which has a detector which is sensitive to the volatile material but which is not significantly sensitive to the desorbing gas;
        3. collecting enough sample data points from sub-step (1) above of the amount of volatile material present in each periodic desorbing gas sample to establish an integrable graphical curve, whether actual or present only in representative form within a computer, the ordinate of which curve representing the total time over which the samples were taken from the desorbing gas and the coordinates of the curve representing the amount of volatile material present in the incremental samples periodically taken from the desorbing gas stream;
        4. integrating the curve to give the total amount of volatile material contained within the non-volatile material; and
        5. dividing the amount of volatile material calculated in sub-step (4) above by the amount of non-volatile material to obtain the solubility of the volatile material in the non-volatile material at the specified temperature and pressure conditions.

2. The method of claim 1 wherein the non-volatile material is a synthetic polymeric material and the volatile material includes an organic material used in the manufacture of the synthetic polymeric material.

3. The method of claim 2 wherein the non-volatile, synthetic, polymeric material is a copolymer of ethylene and an alpha olefin comonomer selected from the group comprised of $C_3$ through $C_{12}$ olefins.

4. The method of claim 2 wherein the organic volatile material is a mixture of hydrocarbon gases used in the manufacture of the non-volatile polymeric material.

5. The method of claim 2 wherein the non-volatile, synthetic, polymeric material is polyethylene and the organic volatile material is ethylene.

6. The method of claim 2 wherein the non-volatile, synthetic, polymeric material comprises a copolymer and the volatile material comprises volatile monomers from which the copolymer is made.

7. The method of claim 6 wherein the copolymer is an ethylene-butene copolymer and the monomers are ethylene and 1-butene.

8. The method of claim 2 wherein the non-volatile, synthetic, polymeric material is polycarbonate.

9. The method of claim 2 wherein the non-volatile, synthetic, polymeric material is selected from the group consisting of polyurethane or an epoxy resin.

10. The method of claim 1 wherein the non-volatile, synthetic, polymeric material is ABS.

11. An apparatus for measuring the solubility of volatile materials in non-volatile materials at desired temperature and pressure conditions, said apparatus being comprised of:
    a. a container which has a gas inlet and a gas outlet, and which has sufficient volume to allow gases to flow through the container while contacting a sample of the non-volatile materials when it is placed in the container;
    b. means for flowing a gaseous saturating stream of the volatile material whose solubility is desired to be determined through the container at the desired temperature and pressure in a manner so as to contact the non-volatile material for a sufficient time for the non-volatile material to become virtually saturated with volatile material from the gaseous saturating stream;

c. means for stopping the flow of the saturating stream through the container;

d. means for flowing a purge gas through the container at a sufficiently large flow rate for a sufficient time to essentially purge the container of any non-sorbed volatile materials remaining therein, but flowing the purge gas in a sufficiently short time so as not to appreciably reduce the amount of volatile materials sorbed by the non-volatile material;

e. means for flowing a desorbing gas stream through the container in a manner and for a time sufficient so that the desorbing gas contacts the non-volatile material for a sufficiently long time so that substantially all of the volatile materials previously sorbed by and contained within the non-volatile material are desorbed from the non-volatile material into the flowing desorbing gas stream, said desorbing gas stream flow being maintained at a known flow rate;

f. means for periodically taking samples of known volume from the desorbing gas stream after it has passed from the container;

g. means for flowing these known small samples of known volumes through a gas chromatograph which has a detector which is sensitive to the volatile material but which is not significantly sensitive to the desorbing gas; and h. means for taking signals from the detector which represent the amount of volatile material being detected by the detector in the desorbing gas and computing the amount of volatile material desorbed from the non-volatile material.

* * * * *